United States Patent
Broeder et al.

(10) Patent No.: US 8,455,650 B2
(45) Date of Patent: Jun. 4, 2013

(54) BENZIMIDAZOLE DERIVATIVE

(75) Inventors: Wolgang Broeder, Ingelheim am Rhein (DE); Rainer Sobotta, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/351,621

(22) Filed: Jan. 17, 2012

(65) Prior Publication Data
US 2012/0116089 A1    May 10, 2012

Related U.S. Application Data

(62) Division of application No. 12/525,867, filed as application No. PCT/EP2008/051397 on Feb. 5, 2008, now Pat. No. 8,119,810.

(30) Foreign Application Priority Data

Feb. 7, 2007 (EP) .................... 07 101 822

(51) Int. Cl.
*C07D 401/12* (2006.01)
(52) U.S. Cl.
USPC .................................... 546/273.7

(58) Field of Classification Search
USPC ........................................ 546/273.4
See application file for complete search history.

(56) References Cited

U.S. PATENT DOCUMENTS
6,414,008 B1 * 7/2002 Hauel et al. ............... 514/394

* cited by examiner

*Primary Examiner* — Patricia L Morris
(74) *Attorney, Agent, or Firm* — Michael P. Morris; Wendy A. Petka

(57) ABSTRACT

The invention relates to a process for preparing the compound of formula 1, a valuable intermediate product in the synthesis of the pharmaceutical active substance dabigatran etexilate.

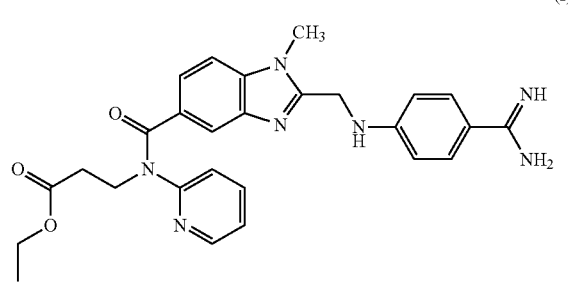

(I)

1 Claim, No Drawings

BENZIMIDAZOLE DERIVATIVE

RELATED APPLICATIONS

This application is a divisional of U.S. application Ser. No. 12/525,867, now U.S. Pat. No. 8,119,810, accorded a 371(c) date of Oct. 2, 2009, which is a 371 of PCT/EP08/51397, filed Feb. 5, 2008, which claims priority to European application no. 07101822, filed Feb. 6, 2007, each of which is hereby incorporated by reference in its entirety.

The invention relates to a process for preparing the compound of formula 1

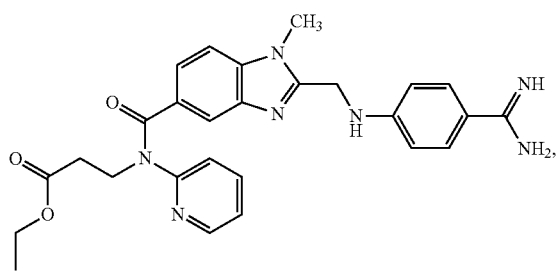

1 a valuable intermediate product in the synthesis of the pharmaceutical active substance dabigatran etexilate.

PRIOR ART

Dabigatran etexilate is known in the prior art and was first disclosed in International Patent Application WO 98/37075. Processes for preparing dabigatran etexilate are also known from WO 2006/000353 or from Hauel et al. (J. Med. Chem., 2002, 45, 1757 ff).

As can be seen from WO 2006/000353, the compound of formula 1 is of central importance in the synthesis of dabigatran etexilate as an intermediate product.

The aim of the present invention is to provide a process which allows for an improved large-scale industrial synthesis of the compound of formula 1.

DETAILED DESCRIPTION OF THE INVENTION

The present invention relates to a process for the large-scale industrial preparation of the compound of formula

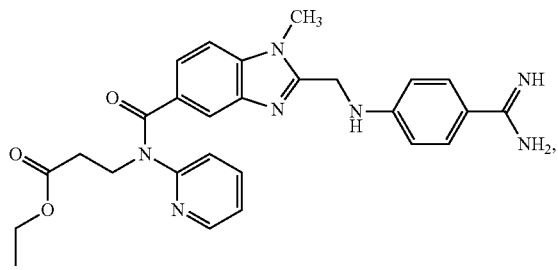

1 optionally in the form of the acid addition salts thereof, preferably in the form of the para-toluenesulphonic acid salt thereof,
characterised in that in a first step a diamine of formula 2

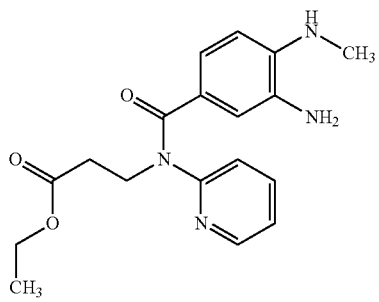

2 is reacted, by means of the carboxylic acid 3

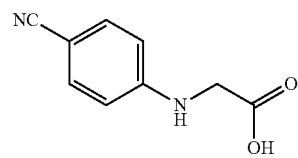

3 in the presence of a suitable coupling reagent, to form a compound of formula 4

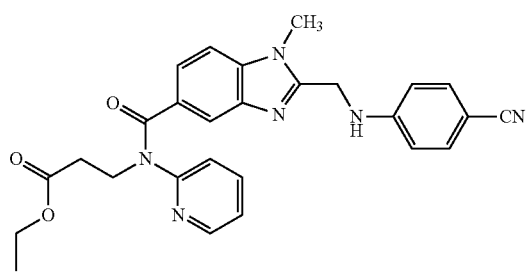

4 which is converted without isolation into the hydrobromide of formula 4-Br

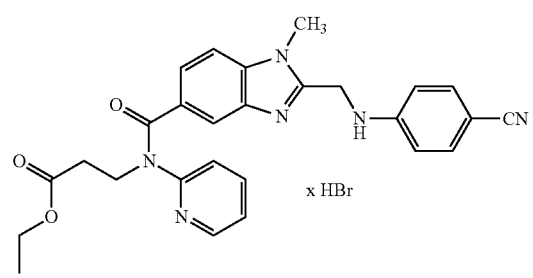

4-Br which is finally converted into the amidine of formula 1.

For reacting the compound of formula 2 to form the compound of formula 4 the following procedure is preferably adopted according to the invention.

The compound of formula 2 is first of all dissolved in a suitable solvent. Suitable solvents according to the invention are preferably solvents selected from the group comprising methylene chloride, dimethylformamide, benzene, toluene, chlorobenzene, tetrahydrofuran, dioxane and mixtures thereof, of which dimethylformamide and tetrahydrofuran are preferred. According to the invention tetrahydrofuran is of particular importance as a solvent at this point.

Preferably 0.5-1 l (liter), particularly preferably 0.65-0.85 l, more preferably 0.7-0.8 l of the above-mentioned solvent is used per mole of the compound of formula 2 used.

Besides the above-mentioned solution another solution is also prepared which contains the carboxylic acid of formula 3 as well as the above-mentioned coupling reagent. For this, according to the invention, the coupling reagent is preferably first of all dissolved in a solvent, which is preferably selected from among the group of solvents mentioned above. Preferably the same solvent is used as is used to dissolve the compound of formula 2. The coupling reagent is preferably selected from among N,N'-dicyclohexylcarbodiimide, N,N'-carbonyldiimidazole and carbonyl-di-(1,2,4-triazole), while N,N'-carbonyldiimidazole and carbonyl-di-(1,2,4-triazole), preferably carbonyl-di-(1,2,4-triazole), are of particular importance according to the invention.

Preferably 1-2 mol, particularly preferably 1-1.5 mol, more preferably 1.05-1.25 mol of is the above-mentioned coupling reagent are used per mol of the compound of formula 2 used. Preferably, 1-3 l, particularly preferably 1.5-2.5 l, more preferably 1.8-2.2 l of the above-mentioned solvent are used, per mol of the compound of formula 2 put in, to dissolve the coupling reagent in the above-mentioned solvent.

The solution of the coupling reagent thus prepared is either stirred at ambient temperature or heated with stirring to a temperature of about 25-50° C., preferably 30-40° C., particularly preferably 32-38° C. and then combined with the compound of formula 3. The addition of the compound of formula 3 preferably takes place batchwise over a period of 0.25 to 4 h (hours), preferably over a period of 0.5 to 3 h, particularly preferably over a period of 1 to 2 h. The addition of the compound 3 is preferably carried out with the existing solution at a constant temperature.

Preferably 1-2 mol, particularly preferably 1-1.5 mol, more preferably 1.05-1.15 mol of the above-mentioned compound of formula 3 are used, per mol of the compound of formula 2 put in.

After the addition of the compound of formula 3 the solution of coupling reagent and 3 thus obtained is optionally stirred for a further period of 0.25 to 4 h (hours), preferably over a period of 0.5 to 3 h, particularly preferably over a period of 0.5 to 1 h. During this time the solution is preferably maintained in one of the above-mentioned temperature ranges, while the temperature is particularly preferably kept constant.

The solution thus obtained is then added to the solution of the compound of formula 2 already prepared. Preferably the solution of compound 2 described above is heated beforehand with stirring to a temperature in the range from about 30-65° C., preferably 40-60° C., particularly preferably 47-53° C.

The solution of coupling reagent and compound 3 prepared is preferably metered into the solution of compound 2 over a period of 0.5-5 h, preferably 1-4 h, particularly preferably 2-3 h. During this time the temperature of the existing solution of compound 2 is preferably kept constant.

After the addition of the solution prepared from 3 and coupling reagent has ended it may optionally be useful to dilute the reaction solution further by the addition of solvent. If more solvent is added, preferably one of the above-mentioned solvents is used, while it is particularly preferable to use the solvent that has already been used to prepare the solution of compound 2.

If the solution is further diluted, preferably 0.1-0.5 l, particularly preferably 0.2-0.3 l of the above-mentioned solvent is used per mol of the compound of formula 2 used.

After the addition of the solution prepared from 3 and coupling reagent has ended and any additional solvent has been added, the solution obtained is stirred for a further period of at least 1 to 8 h (hours), preferably at least 2 to 7 h, particularly preferably at least 3 to 6 h. The solution is preferably kept within one of the above-mentioned temperature ranges, and particularly preferably the temperature is kept constant.

Then large amounts of the solvent are optionally distilled off under reduced pressure. Particularly preferably, 1-1.8 l, particularly preferably 1.2-1.7 l, more preferably 1.4-1.5 l of the above-mentioned solvent is eliminated by distillation, per mol of compound 2 used.

The distillation of the solvent is preferably carried out in a temperature range of about 40-65° C., particularly preferably at 50-60° C. If it is not possible to distil off the solvent at normal pressure within this temperature range on account of the choice of solvent, the pressure is lowered until distillation takes place successfully within the temperature range specified.

It may optionally be advantageous to entrain any residual amounts of the solvent originally used which are present in the distillation residue by adding another solvent. If for example tetrahydrofuran is used as solvent for the reaction described hereinbefore, the use of n-butyl acetate has proved advantageous. If n-butyl acetate is used at this point it is distilled off together with the tetrahydrofuran under reduced pressure at a temperature of about 50-85° C. The distillation is carried out such that the tetrahydrofuran used previously is almost totally removed and only n-butyl acetate remains as solvent. After distillation is complete the remaining solution is combined with acetic acid. Preferably, concentrated acetic acid is used at this point, particularly glacial acetic acid (approx. 99% acetic acid).

Preferably 100-200 g (grams), particularly preferably 120-170 g, more preferably 130-145 g of the above-mentioned concentrated acetic acid are used, per mol of the compound of formula 2 used.

Then the mixture is heated with stirring to a temperature in the range from about 65-100° C., particularly preferably 75-95° C., particularly preferably 85-90° C. and stirred at least over a period of 0.5-5 h, preferably 1-4 h, particularly preferably 2-3 h at constant temperature.

Then the mixture is preferably brought to a temperature in the range from about 45-85° C., preferably 55-80° C., particularly preferably 65-75° C. and mixed with water for further working up. Particularly preferably, 0.5-2 l, particularly preferably 0.75-1.5 l, more preferably 0.9-1.1 l of water are added, per mol of the compound of formula 2 used.

Optionally, aqueous NaCl solution is also added, besides water. If NaCl is also added, preferably 20-80 g (grams), particularly preferably 30-60 g, more preferably 40-50 g NaCl are used, per mol of the compound of formula 2 used.

The phase mixture thus obtained is mixed thoroughly and the aqueous phase is separated off using conventional methods. Optionally the phase separated off is extracted again with the organic solvent used previously. The solvent is removed from the organic phases by distillation under reduced pressure.

The distillation of the solvent is preferably carried out in a temperature range of below 80° C., preferably at about 60-80° C., particularly preferably at 70-80° C. If it is not possible to distil off the solvent at this temperature range under normal pressure on account of the choice of solvent, the pressure is lowered until the distillation takes place successfully within the temperature range specified.

The distillation residue remaining contains the compound of formula 4, which is further reacted directly, according to the invention, without being isolated, using the procedure described below, to obtain the compound of formula 4-Br.

The distillation residue is combined with an alcohol, preferably with ethanol or isopropanol, particularly preferably isopropanol, and optionally heated slightly.

Preferably, 0.5-3 l, particularly preferably 1-2.5 l, more preferably 1.5-2 l of the above-mentioned alcohol are added per mol of the compound of formula 2 used.

If the resulting mixture is heated, a temperature of preferably about 25-50° C., preferably 30-40° C., particularly preferably 32-38° C. is selected.

Then aqueous hydrobromic acid is added. It is particularly preferable to use concentrated aqueous hydrobromic acid. For example, 48% aqueous hydrobromic acid may be used. Sufficient hydrobromic acid is added at constant temperature, with stirring, until the pH of the mixture obtained is less than 3, preferably less than 2, and particularly preferably is in the range between pH 0.6-1.3. Using the 48% hydrobromic acid mentioned hereinbefore by way of example, 0.1-0.3 kg, preferably 0.15-0.25 kg, particularly preferably 0.17-0.21 kg hydrobromic acid (48%) may be added per mol of the compound of formula 2 used.

After the addition of the hydrobromic acid has ended the mixture obtained is stirred for a further period of at least 5 to 60 min (minutes), preferably at least 10 to 45 min, particularly preferably at least 20 to 30 min. During this time the solution is preferably maintained in one of the above-mentioned temperature ranges, while the temperature is particularly preferably kept constant. Then the resulting mixture is preferably cooled to a temperature in the range from 0 to 20° C., preferably 5 to 15° C., particularly preferably 7-13° C. and stirred at this temperature for a further period of at least 0.5 to 2 h (hours), preferably at least 0.75 to 1.5 h, particularly preferably at least 1 h.

The resulting suspension of 4-Br in alcohol is then freed from the solvent by centrifuging and the residue remaining is optionally washed with one of the above-mentioned alcohols. The 4-Br obtained is then dried in vacuo at a temperature of not more than 30-65° C., preferably not more than 50-60° C.

The present invention further relates to the hydrobromide of formula 4-Br

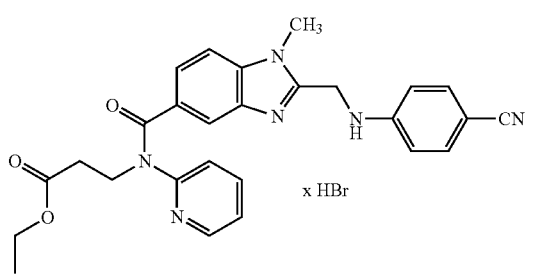

4-Br thus obtained as such. Surprisingly it has been found that this salt of the compound of formula 4 is particularly easy to separate off, which makes it significantly simpler to isolate this intermediate product during reactions on an industrial scale. By ease of separation is meant, within the scope of the present invention, the ability to free the resulting crystalline product from the solvent by filtration, suction filtering, centrifuging or comparable methods of isolation. An improvement to the separation qualities has a direct effect on the throughput of the process and is therefore of exceptional importance, particularly when carrying out reactions on an industrial scale. The product, having better separation qualities, can be isolated faster, washed faster and better and hence dried faster as well.

The compound of formula 1 may be obtained from the compound 4-Br using the following procedure.

4-Br is first of all preferably added to an organic solvent mixed with a suitable acid. The acid is preferably hydrochloric acid according to the invention and the solvent is preferably an alcohol. Particularly preferably, isopropanol or ethanol, particularly preferably ethanol is used. It has proved particularly preferable according to the invention to use 5-12 molar, particularly preferably 9-11 molar ethanolic hydrochloric acid. If, as is particularly preferred according to the invention, 10 molar ethanolic hydrochloric acid is used, preferably 0.4-1.5 kg, preferably 0.6-1.0 kg, particularly preferably 0.75-0.85 kg of the 10 molar ethanolic hydrochloric acid are used per mol of the compound 4-Br used.

4-Br is preferably added to the acid-containing alcohol according to the invention at a temperature in the range from about 20-25° C., preferably at ambient temperature (23° C.), with stirring. Preferably, according to the invention, the compound of formula 1 is prepared in the form of an acid addition salt. Particularly preferably the compound of formula 1 is prepared in the form of its para-toluenesulphonic acid salt. If the compound of formula 1 is to be obtained as a paratoluenesulphonic acid addition salt, it has proved advantageous to add the para-toluenesulphonic acid at this stage. Accordingly, after the addition of the solution of 4-Br to the above-mentioned, preferably hydrochloric, acid-containing alcohol, p-toluenesulphonic acid is also added. The para-toluenesulphonic acid is preferably added in the form of its hydrate.

Alternatively to the procedure described above, all the para-toluenesulphonic acid may be added first, before the compound 4-Br is added to the acid-containing alcohol. Preferably 180-300 g (grams), particularly preferably 200-300 g, more preferably 245-255 g of the above-mentioned aqueous p-toluenesulphonic acid may be added per mol of the compound of formula 4-Br used.

After the addition has ended the mixture is preferably adjusted, with stirring, to a temperature in the range from about 23-40° C., preferably 25-35° C., particularly preferably 28-29° C. and stirred for a further period of at most 12-36 h, preferably at most 20-28 h, particularly preferably at most 23-25 h at constant temperature.

It may then optionally be sensible to dilute the reaction solution further by the addition of solvent. If more solvent is added, preferably one of the above-mentioned alcohols is used, while it is particularly preferable to use the particular alcohol that has already been used to prepare the solution of the compound 4-Br. Accordingly, ethanol is preferably used here as well.

If the solution is diluted further, preferably 0.5-1.5 l, particularly preferably 0.8-1.0 l of the above-mentioned solvent, preferably alcohol, particularly preferably ethanol is used per mol of the compound of formula 4-Br used.

Then the mixture is cooled with stirring to a temperature in the range from about −10 to 15° C., preferably −5 to +5° C., particularly preferably 1 to 3° C. and combined with aqueous ammonia solution. It is particularly preferable to use 20-30%, preferably 20-25% ammonia solution, while 25% aqueous ammonia solution is preferably used according to the invention. If 25% aqueous ammonia solution is used, preferably 0.5-1.5 kg, particularly preferably 0.6-1.0 kg, more preferably 0.7-0.8 kg of the above-mentioned 25% aqueous ammonia solution are used per mol of the compound of formula 4-Br used.

The aqueous ammonia solution is preferably added such that the temperature is maintained in the range from about 0-15° C., preferably 0-10° C. Particularly preferably the addition is controlled so that the temperature remains constant. The pH of the solution preferably rises to a range of 9-10.5, preferably to pH 9.3-10.

After the addition has ended the mixture is preferably heated with stirring to a temperature in the range from about 20-30° C., preferably 22-27° C., particularly preferably about 25° C. and stirred for a further period of at least 2-8 h, preferably at least 2.4-6 h, particularly preferably at least 3-5 h at constant temperature.

Then large amounts of the solvent are optionally distilled off under reduced pressure. Particularly preferably, 0.2-0.8 l, particularly preferably 0.3-0.7 l, more preferably 0.4-0.5 l of the above-mentioned solvent is eliminated by distillation, per mol of compound 4-Br used.

The distillation of the solvent is preferably carried out in a temperature range of about 40-65° C., particularly preferably at 50-60° C., If it is not possible to distil off the solvent at normal pressure within this temperature range on account of the choice of solvent, the pressure is lowered until distillation takes place successfully within the temperature range specified.

Then the mixture is mixed with water at constant temperature (about 50-60° C.) for further working up. Particularly preferably, 2-8 l, particularly preferably 4-7 l, more preferably 5-6 l water are added per mol of the compound 4-Br used. Besides the addition of water, aqueous NaOH solution, preferably 30-60%, particularly preferably 40-50% NaOH solution is also added. It is particularly preferable according to the invention to add 50% aqueous NaOH solution.

If 50% NaOH solution is added, preferably 50-200 ml, particularly preferably 70-150 ml, more preferably 90-110 ml of 50% NaOH solution are added per mol of the compound 4-Br used.

After the addition has ended the mixture is preferably adjusted to a temperature in the range from about 40-70° C., preferably 50-60° C., particularly preferably about 55° C. with stirring and stirred for a further period of at least 0.5-1.5 h, preferably at least 0.6-1.25 h, particularly preferably at least 0.75-1 h at constant temperature.

The mixture is then optionally cooled to a temperature in the range from about 0-30° C., preferably 5-20° C., particularly preferably 10-15° C. and stirred for a further period of at least 0.5-2 h, preferably at least 0.75-1.5 h, particularly preferably at least 1 h at constant temperature.

The crystals obtained are separated off, washed with water and optionally an organic solvent and then dried in vacuo at a temperature of not more than 50-90° C., preferably not more than 60-70° C.

The following Examples serve to illustrate a synthesis process carried out by way of example. They are intended solely as examples of possible procedures without restricting the invention to their contents.

EXAMPLE 1

Large-Scale Industrial Synthesis of the Compound of Formula 4-Br 88 kg carbonyl-di-(1,2,4-triazole) are taken and combined with 920 l tetrahydrofuran. The contents of the apparatus are heated to 35° C. with stirring. Then 90 kg of compound 3 are added batchwise at 35° C. within 1 to 2 hours.

160 kg of compound 2 are placed in a second reaction vessel, then 350 l tetrahydrofuran are added and the mixture is heated to 50° C. with stirring.

The solution of 3 is metered into the solution of 2 within 2 to 3 hours at 47° C.-53° C. and the solution obtained is diluted with 115 l tetrahydrofuran.

Then the mixture is stirred for another 4 hours at 47° C.-53° C. (preferably 50° C). Then 670 l-695 l tetrahydrofuran are distilled off in vacuo at 50° C.-60° C. 235 l of n-butyl acetate are then allowed to flow into the residue. After this, 600 l-630 l of a butyl acetate/THF mixture are distilled off in vacuo at 50° C.-85° C. During the distillation 700 l butyl acetate are metered in.

65 kg acetic acid are allowed to flow into the residue, the contents are heated to 85° C.-90° C. and stirred for at least another 2.5 h at this temperature. Then the mixture is cooled to 65° C.-75° C. A solution of 165 l water and 20 kg common salt is added to the contents and the mixture is rinsed with 300 l water. Then the temperature is adjusted to 60° C.-70° C. and the mixture is stirred for a minimum of 15 min. at this temperature. For phase separation the stirrer is stopped and the mixture is left to settle for at least 15 min. The aqueous phase is drained off into another reaction vessel which contains 120 l of n-butyl acetate. The mixture is heated to 60° C.-70° C. with stirring and stirred for at least 10 min. After phase separation the aqueous phase is drained off into the chemical waste drain. The butyl acetate phases and 20 l of butyl acetate for rinsing are combined. 590 l-620 l of n-butyl acetate are distilled off from this content in vacuo at a max, internal temperature of 80° C. 880 l isopropanol are allowed to flow into the distillation residue and the content is adjusted to 32° C.-38° C. Then approx. 90 kg of 48% hydrobromic acid are metered in at 32° C.-38° C. until the pH value is 0.6 to 1.3. The mixture is stirred for a minimum of 20 min. at 32° C.-38° C. and then cooled to 7° C.-13° C. and stirred at this temperature for at least one hour. The resulting suspension is centrifuged, washed with a total of 840 l isopropanol and dried in vacuo at max. 55° C.

Yield: 211 kg-250 kg. M.p.: 200-215° C. (with decomposition).

The compound 4-HBr may be isolated using any standard commercially available centrifuge.

EXAMPLE 2

Large-Scale Industrial Synthesis of the Compound of Formula 1 (in the Form of the Para-Toluenesulphonate Acid Addition Salt)

330 kg of compound 4-Br and 147 kg p-toluenesulphonic acid (aqueous) are added with stirring to 470 kg of 10 molar ethanolic hydrochloric acid at 23° C. Then the mixture is heated to 28° C.-29° C. and stirred for 23 h at this temperature. The reaction mixture is diluted with 693 l ethanol and transferred into a second reaction vessel. The contents of this reaction vessel are diluted with another 536 l ethanol and cooled to 2° C. 440 kg of 25% ammonia solution are metered in, with the temperature maintained at around 10° C., until a pH of 9.3 to 10 is obtained, with further cooling and stirring. The contents of the apparatus are heated to 25° C. and stirred for 4 hours at this temperature. Then the contents are heated to 50 to 60° C. and 248 l-261 l of ethanol are distilled off in vacuo. Then 1220 l of water are added at an internal temperature of 50° C.-60° C. The contents of the apparatus are divided between two reaction vessels of the same size in equal amounts (approx. 1450 l). Processing is continued in parallel (simultaneously) in both apparatus.

In each case a solution of 950 l water and 31 l sodium hydroxide solution (50%) is added. The contents of the two apparatus are adjusted to a temperature of 50 to 60° C. (preferably 55° C.) and stirred for 45 min. Then within 3 h the mixture is cooled to 10° C.-15° C. and stirred for a further 60 min. at this temperature.

The crystal suspensions are separated off through two centrifuges. The product is washed first of all with water, then with acetone and then dried in vacuo to a max. Temperature of 70° C.

Yield: 314 kg-371 kg; melting point: 209-211° C.

The invention claimed is:
1. Compound of formula 4-Br

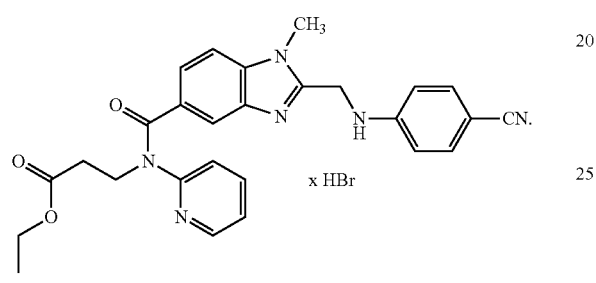

* * * * *